(12) United States Patent
Simakov et al.

(10) Patent No.: US 10,982,342 B2
(45) Date of Patent: Apr. 20, 2021

(54) DEVICE AND METHOD FOR DETERMINING THE COMPOSITION OF AN ELECTROLYTE

(71) Applicant: United Company RUSAL Engineering and Technology Centre LLC, g. Krasnoyarsk (RU)

(72) Inventors: Dmitrij Aleksandrovich Simakov, Krasnoyarsk (RU); Aleksandr Olegovich Gusev, Krasnoyarsk (RU); Kirill Borisovich Bakin, Krasnoyarsk (RU); Aleksandr Viktorovich Dontsov, Krasnoyarsk (RU)

(73) Assignee: United Company RUSAL Engineering and Technology Centre LLC, Krasnoyarsk (RU)

( * ) Notice: Subject to any disclaimer, the term of this patent is extended or adjusted under 35 U.S.C. 154(b) by 18 days.

(21) Appl. No.: 16/307,869

(22) PCT Filed: May 30, 2017

(86) PCT No.: PCT/RU2017/000368
§ 371 (c)(1),
(2) Date: Dec. 6, 2018

(87) PCT Pub. No.: WO2017/213553
PCT Pub. Date: Dec. 14, 2017

(65) Prior Publication Data
US 2020/0080213 A1    Mar. 12, 2020

(30) Foreign Application Priority Data
Jun. 8, 2016  (RU) ............................ RU2016122695

(51) Int. Cl.
*G01N 25/00* (2006.01)
*C25C 3/20* (2006.01)
(Continued)

(52) U.S. Cl.
CPC ............... *C25C 3/20* (2013.01); *C25C 3/18* (2013.01); *G01N 1/125* (2013.01); *G01N 25/4866* (2013.01); *G01N 33/205* (2019.01)

(58) Field of Classification Search
CPC .. G01N 25/4866; G01N 33/205; G01N 25/04; G01N 1/125; G01N 33/20;
(Continued)

(56) References Cited

U.S. PATENT DOCUMENTS

| 2,464,267 | A | * | 3/1949 | Short ........................ | C25C 3/18 |
|  |  |  |  |  | 205/392 |
| 4,469,649 | A | * | 9/1984 | Ibar ........................ | B29C 43/00 |
|  |  |  |  |  | 264/237 |

(Continued)

FOREIGN PATENT DOCUMENTS

| GB | 008527305 | * | 12/1985 | |
| JP | 60058549 A | * | 4/1985 | ......... G01N 27/4074 |

(Continued)

OTHER PUBLICATIONS

International Search Report dated Oct. 19, 2017 issued in PCT/RU2017/000368.

*Primary Examiner* — Gail Kaplan Verbitsky
(74) *Attorney, Agent, or Firm* — Hogan Lovells US LLP (57) ABSTRACT

This invention relates to nonferrous metallurgy, in particular to a device and method for electrolyte composition analysis based on differential thermal measurements for aluminum electrolysis control. The device is comprised of a metal body including a reference material and an electrolyte sample receptacle, temperature sensors immersed into the reference material and in an electrolyte sample, a system for registration, data processing, and visualization of obtained results. A method includes immersing a metal body into an electrolyte; filling a receptacles with the molten electrolyte; removing and cooling down the metal body having the filled (Continued)

receptacle above a crust on the molten electrolyte surface; drawing and analyzing differential-thermal curves based on which the liquidus temperature, electrolyte superheating and phase and blend compositions of electrolyte solid samples are determined taking into account all crystallizing phases the content of which in the electrolyte sample is no less than 3 wt %.

9 Claims, 7 Drawing Sheets

(51) Int. Cl.
  *C25C 3/18* (2006.01)
  *G01N 33/205* (2019.01)
  *G01N 1/12* (2006.01)
  *G01N 25/48* (2006.01)

(58) Field of Classification Search
  CPC .... G01N 27/4162; G01N 25/00; G01K 13/00; B22F 2203/11; C25C 3/20
  USPC ............... 374/10–12, 16, 30–39, 45, 139; 702/23–25, 30
  See application file for complete search history.

(56) References Cited

U.S. PATENT DOCUMENTS

| | | | |
|---|---|---|---|
| 4,925,749 A * | 5/1990 | Wright | H01M 10/39 429/104 |
| 5,033,320 A * | 7/1991 | Baerts | G01N 1/125 73/864.59 |
| 5,752,772 A | 5/1998 | Verstreken et al. | |
| 6,220,748 B1 * | 4/2001 | Bates | G01K 13/125 374/10 |
| 6,942,381 B2 * | 9/2005 | Hosier | C25C 3/20 374/139 |
| 7,112,269 B2 * | 9/2006 | Slaugenhaupt | C25C 3/20 205/336 |
| 7,811,478 B2 * | 10/2010 | Yoshida | H01M 4/131 252/182.1 |
| 9,377,370 B2 * | 6/2016 | Kim | G01K 17/00 |
| 10,087,075 B2 * | 10/2018 | Nakayama | D01F 1/07 |
| 10,386,423 B2 * | 8/2019 | Day | H01M 10/486 |
| 2003/0193988 A1 | 10/2003 | Bates | |
| 2009/0008602 A1 * | 1/2009 | Yoshida | H01M 4/366 252/182.1 |
| 2010/0089118 A1 * | 4/2010 | Mayer | G01N 27/18 73/1.16 |
| 2012/0250723 A1 * | 10/2012 | Blumm | G01N 25/4813 374/13 |
| 2013/0213808 A1 * | 8/2013 | Yang | G01N 27/301 204/435 |
| 2018/0217010 A1 * | 8/2018 | Umkehrer | G01K 7/38 |

FOREIGN PATENT DOCUMENTS

| | | |
|---|---|---|
| RU | 2026391 C1 | 1/1995 |
| RU | 2303246 C1 | 7/2007 |
| RU | 2323423 A | 11/2007 |
| SU | 315955 A | 10/1971 |
| WO | 2012106291 A2 | 8/2012 |

* cited by examiner

DEVICE AND METHOD FOR DETERMINING THE COMPOSITION OF AN ELECTROLYTE

CROSS-REFERENCE TO RELATED APPLICATIONS

This application is a U.S. National Phase under 35 U.S.C. § 371 of International Application PCT/RU2017/000368, filed on May 30, 2017. All publications, patents, patent applications, databases and other references cited in the International Application PCT/RU2017/000368, filed on May 30, 2017, all related applications referenced herein, and all references cited therein, are incorporated by reference in their entirety as if restated here in full and as if each individual publication, patent, patent application, database or other reference were specifically and individually indicated to be incorporated by reference.

FIELD OF THE INVENTION

This invention relates to nonferrous metallurgy, in particular to the electrolytic production of aluminum, namely to a device and method for electrolyte composition analysis based on differential thermal measurements for aluminum electrolysis control.

Currently, aluminum is produced by electrolytic reduction of alumina dissolved in an electrolyte that is molten fluorides. One of its most important advantages for the technical and economic performance of electrolysis is an electrolyte composition. Composition control is performed by periodical sampling, wherein samples are then analyzed in the lab. It takes a few hours to a few days from the point of sampling to the point when analysis results become available, that is why the analysis results are not always relevant to make technological decisions. The control of electrolysis is often achieved by means of methods of the quick analysis of liquidus temperature, superheating, and electrolyte composition, which are based on the use of thermal or differential thermal analysis of electrolyte sample cooling curves. When the differential thermal analysis is applied, a differential thermal curve representing a temperature difference between a sample and a reference material shall be drawn.

BACKGROUND

The known methods and devices (U.S. Pat. No. 5,752,772, C25C 3/20, published on 19 May 1998, RU Patent No. 2303246, G01K7/02, published on 20 Jul. 2007) are based on standardless measurement of electrolyte liquidus temperature which includes registration and analysis of an electrolyte cooling curve only in a certain temperature range. This makes it possible to determine the liquidus temperature and the electrolyte superheating value; however, it doesn't provide any insight into the composition of the electrolyte of interest, which is the main drawback of the standardless analysis.

The U.S. Pat. No. 5,752,772, for example, describes a sensor from Heraeus Electro-Nice configured for electrolyte temperature and liquidus temperature measurement, A replaceable (disposable) sensing tip of this sensor consists of a metal dipper arranged inside a cardboard tube, and a thermocouple arranged inside the dipper. After pre-heating above the melt, a probe is immersed into an electrolyte and its temperature is measured. The electrolyte sample in the dipper is removed from the melt. When cooling down, a cooling curve of the electrolyte sample (from the electrolyte melt temperature to its liquidus temperature) is registered. The electrolyte liquidus temperature is determined from the abrupt change of the sample cooling curve slope. One of the drawbacks of the device is the fact that the tip cannot be reused. In addition, an increase in a number of melt components leads to a decrease in accuracy of a melt liquidus temperature determination and, accordingly, of electrolyte superheating value. The device is quite cumbersome, and in order to move it along the body, a trolley is typically used.

A device and a method described in RU Patent 2303246 are characterized by the use of a reusable electrolyte sampler. Prior to extracting a collected electrolyte sample, the sampler is heated up to the melt temperature. Sample cooling down to the liquidus temperature is performed on the electrolyte crust, and the electrolyte liquidus temperature is determined at the time of evolution of the maximum heat of crystallization as the greatest value of the second derivative of the electrolyte temperature from the range of smoothed values of electrolyte cooling curve. Once the liquidus temperature has been determined, the sampler is washed by oscillating movements in the electrolyte melt and is cleaned-up from the melt residues. One of the drawbacks of the device is the principle of melt liquidus temperature determination. The determination of electrolyte liquidus temperature at the time of evolution of the maximum heat of crystallization is associated with errors made during the transition to electrolyte systems where the electrolyte liquidus is defined by low concentrated phases and, correspondingly, low heat effect.

Electrolyte composition can be determined with devices described in U.S. Pat. No. 6,220,748, IPC G01N25/00, published on 24 Apr. 2001, and U.S. Pat. No. 6,942,381, C25C 3/20, published on 31 Mar. 2005.

U.S. Pat. No. 6,220,748 describes a method and a device for electrolyte composition analysis. The method allows determining the electrolyte cryolite ratio and the alumina concentration. The device comprises an open cup to collect an electrolyte sample and a closed receiving cup for the reference material, each of which is fitted with thermocouples. These cups are supported by a hollow metal cylinder and are separated from each other in space.

Based on the measurement results, the electrolyte temperature, liquidus temperature and electrolyte superheating are determined. In order to determine the cryolite ratio and the alumina concentration, a differential thermal curve is used. This electrolyte cryolite ratio is determined based on the arrangement and size of peaks on the differential thermal curve. Alumina content as a function of a peak area on the differential thermal curve at the temperature range 400-500° C. The device has a complex design, the drawback of which is a spatial separation of test and reference samples. In this case, their cooling down is performed under different thermal conditions leading to a significant decrease in measurement accuracy and, accordingly, in an accuracy of electrolyte composition analysis results.

A method and device according to U.S. Pat. No. 6,942,381 are the closest analogs of the claimed device and method in terms of its technical specs and effectiveness. The device for implementing the method according to U.S. Pat. No. 6,942,381 comprises a reusable one-piece metal body including a reference material and an electrolyte sample receptacle, as well as thermocouples immersed in the reference material and the electrolyte sample, a system for registration, data processing, and visualization of obtained results. The method for molten electrolyte composition analysis includes immersing the metal body into an electrolyte; filling the receptacle with the electrolyte melt; removing and cooling down the metal body with the filled receptacle; drawing and analyzing differential thermal curves to determine the liquidus temperature, superheating, and electrolyte composition. The method allows determining the industrial electrolyte cryolite ratio and the alumina concentration. The cryolite ratio and the alumina concentration are determined based on a peak area on a differential thermal curve in the temperature range 850-930° C. and 650-700° C. Alumina content as a function of a peak area on the differential thermal curve at the temperature range 800-900° C. Once the measurement is finished, the device is washed in the melt. The drawback of the device and the method is the use as a reference material the material of the device. To achieve the distinct peaks of electrolyte phase crystallization and, accordingly, the consistent and repeatable results of melt composition analysis, the heat exchange between an electrolyte sample and a reference material should be at the minimum. The negative effect of heat exchange is expressed by the fact that the heat effects of phase transformations in an electrolyte sample will be registered on the reference material cooling curve, as the result of which peak identification on the thermal and differential-thermal curves, as well as analysis of phase concentrations in an electrolyte, will be more difficult. This is especially important for low concentrated phases in an electrolyte because exactly these phases can represent the melt liquidus temperature. All mentioned above limits the scope of application of the device and method to cryolite-alumina melts with a cryolite ratio above 2 and constrains its usage in acidic, multicomponent (modified) electrolytes, as well as in melts having an alumina concentration close or equal to the saturation concentration.

SUMMARY OF THE INVENTION

The technical problem the present invention is aimed to address consists in the improvement of electrolyte composition analysis accuracy, thus, allowing creating conditions for maintaining the cryolite-alumina melt compositions used for aluminum production stable.

The claimed device, as the device for molten electrolyte composition analysis according to U.S. Pat. No. 6,942,381, includes a metal reusable body comprising a reference material, at least one electrolyte sample receptacle, temperature sensors immersed into the reference material and an electrolyte sample, a system for registration, data processing, and visualization of obtained results which is in communication with the temperature sensors.

The technical problem is addressed with the attained technical effect that is comprised in determining electrolyte phase and blend compositions and in measurement reliability improvement.

The technical problem is addressed by using an α-modification of aluminum oxide as a reference material arranged within a metal body compartment.

The device is complemented with particular embodiments, which make it possible to improve the accuracy of electrolyte composition analysis.

In particular, the device can comprise from one to four electrolyte sampling receptacles, wherein if the number of receptacles is more than one they are arranged on either side of the reference material.

Thermocouples are typically used as temperature sensors of the device.

For stable operation, a temperature sensor immersed into the reference material is protected with a corundum cover.

Moreover, the device can comprise a metal protective tube rigidly connected to the metal body around the periphery of the reference material compartment, wherein holders and fixing members for the temperature sensors to be immersed directly into the electrolyte sampling receptacles are arranged on said tube.

Electrolyte temperature sensors can be arranged within the metal tube rigidly connected to the metal body, wherein the metal tube is connected, via through-channels made in the metal body, to the electrolyte sampling receptacles for enabling immersion of temperature sensors into the electrolyte sampling receptacles.

The technical problem is also addressed with the attained technical effect due to the fact that a method for molten electrolyte composition analysis according to the claimed invention which includes immersing a device into an electrolyte; filling sampling receptacles with electrolyte; removing and cooling down the device having filled receptacles; drawing and analyzing thermal and differential-thermal curves; determining the liquidus temperature, superheating and electrolyte composition, when analyzing thermal and differential-thermal curves these curves are divided into peaks; a phase peak height and/or area and/or half-width is determined; phase concentration in the electrolyte is determined based on the calibration dependence at least on one of the parameters of the phase peak; phase and blend compositions of electrolyte solid samples are determined taking into account all crystallizing phases the content of which in the electrolyte sample is no less than 3 wt %.

The method can be characterized by that after sampling the device is cooled down above a crust on the molten electrolyte surface.

Compared to U.S. Pat. No. 6,942,381, the device has following differences:

Firstly, it is suggested to use as a reference material a substance that is different from the device material, namely an α-modification of aluminum oxide. This will significantly reduce the heat exchange between a sample and a reference material, and accordingly will increase the device response, measurement reliability and electrolyte composition analysis stability, regardless the number of electrolyte sampling receptacles.

Secondly, it is suggested to increase the number of electrolyte sampling compartments up to 2-4 which will make it possible to register at the same time 2-4 electrolyte cooling curves, thus, even more improving the measurement accuracy and reducing the measurement cycle time since, among other things, there would no need to repeat the measurement if one of the thermocouples failed.

Thirdly, it is suggested to protect a thermocouple immersed into a reference material with a corundum cover. This measure makes it possible to exclude a possible contact between a thermocouple immersed into a reference material and a device material, and thus to reduce its heat effect on readings of the thermocouple immersed into the reference material, and to protect the thermocouple from damages if the electrolyte enters the reference material.

Fourthly, during measurements, calibrated thermocouples of type K or S are used as temperature sensors. Thermocouples are selected based on operating conditions and accuracy factors required.

Fifthly, there are two options how to mount thermocouples immersed into an electrolyte sample—open and closed. Both these options include quick replacement of a failed thermocouple, which significantly increases device lifetime.

Compared to U.S. Pat. No. 6,942,381, the claimed method has following differences:

Firstly, complete phase and blend compositions of electrolyte solid samples are determined taking into account all crystallizing phases the content of which in the electrolyte sample is no less than 3 wt %, which enables using the method for analysis of any molten electrolyte system compositions.

Secondly, a device metal body is cooled down above the electrolyte crust, which results in diminished influence of external conditions on the cooling rate of the device metal body and enables more distinct peaks of electrolyte phase crystallization.

The method consists in differential-thermal measurements followed by obtained curves analysis, as a result of which phase and blend compositions of electrolyte solid samples are determined taking into account all crystallizing phases the content of which in the sample is no less than 3 wt %.

BRIEF DESCRIPTION OF THE FIGURES

The essence of the invention will be better understood upon studying following figures, where.

DETAILED DESCRIPTION OF THE INVENTION

Figure 1:
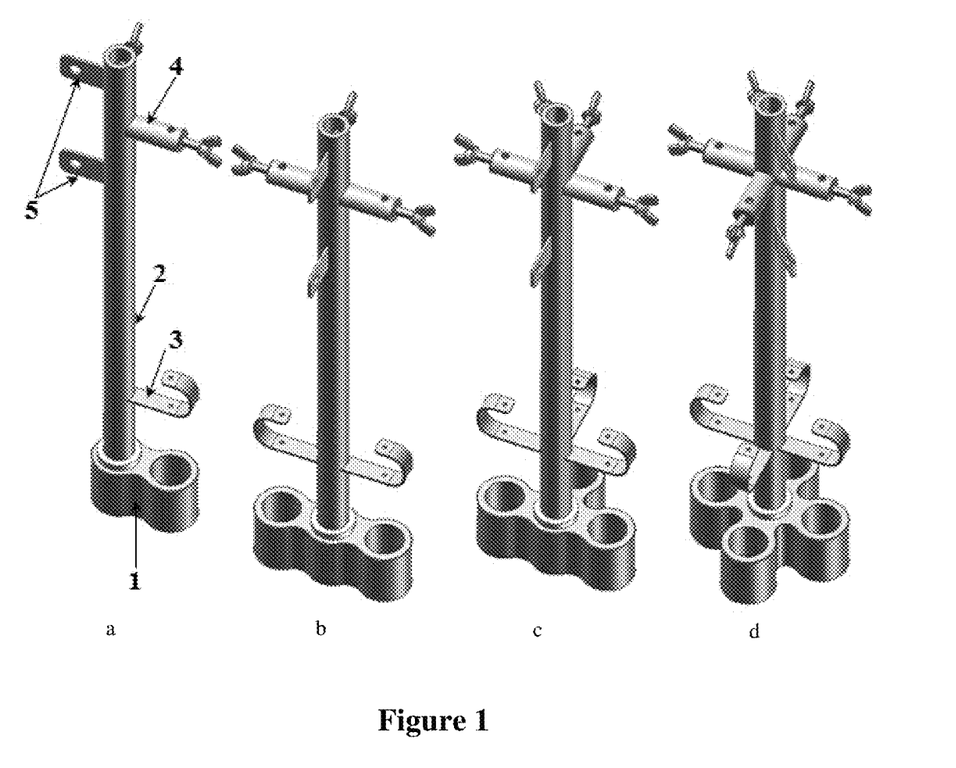
FIGS. 1a, 1b, 1c, 1d show embodiments of a device having different number of electrolyte sampling receptacles.
Figures 2, 3:
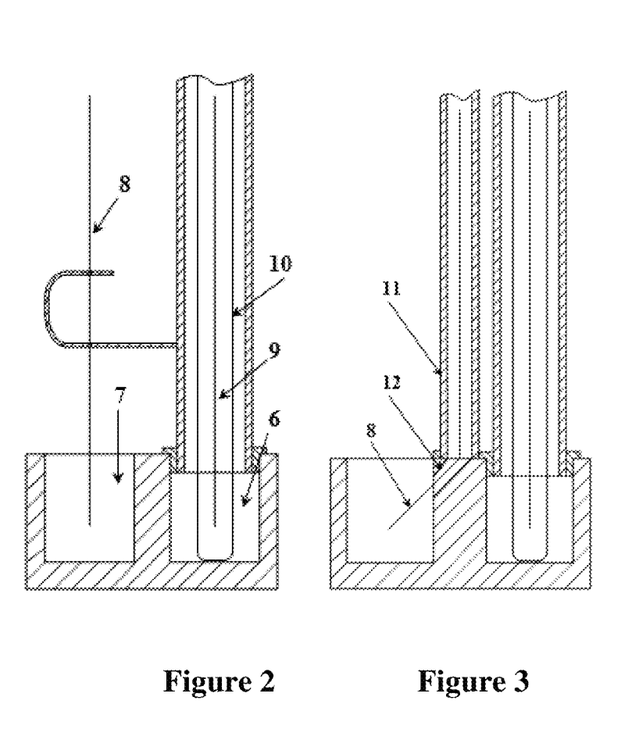
FIG. 2 shows a cross-section of a device for electrolyte composition analysis having one metal protective tube.
FIG. 3 shows a cross-section of a device for electrolyte composition analysis having two metal protective tubes, FIG. 4 schematically shows a device for electrolyte composition analysis.

A device consists of following main components (FIG. 1, 2): a metal body 1, a metal protective tube 2 on which a thermocouple holder 3 and an electrolyte sample thermocouple fixing member 4 are arranged. The metal tube 2 comprises fixturing elements 5. Inside the metal body, there is a compartment for a reference material 6 on either side of which electrolyte receptacles 7 are located. The metal body 1 and the tube 2 are rigidly interconnected by means of a welded connection. The device comprises a thermocouple 8 immersed into an electrolyte sample receptacle and a thermocouple 9 placed into a corundum cover 10 placed within the compartment for reference material. It should be noted that other alternative designs of the device differ by the presence of additional electrolyte receptacles and additional holders and fixing members for a thermocouple immersed into an electrolyte sample receptacle. Moreover (FIG. 3), thermocouples, which register electrolyte sample 8 temperature, can be arranged inside a metal tube 11 and can extend into the electrolyte sample receptacle via a through-channel 12. All structural elements of the device are made of the same material—heat-resistant steel.

Figure 4:
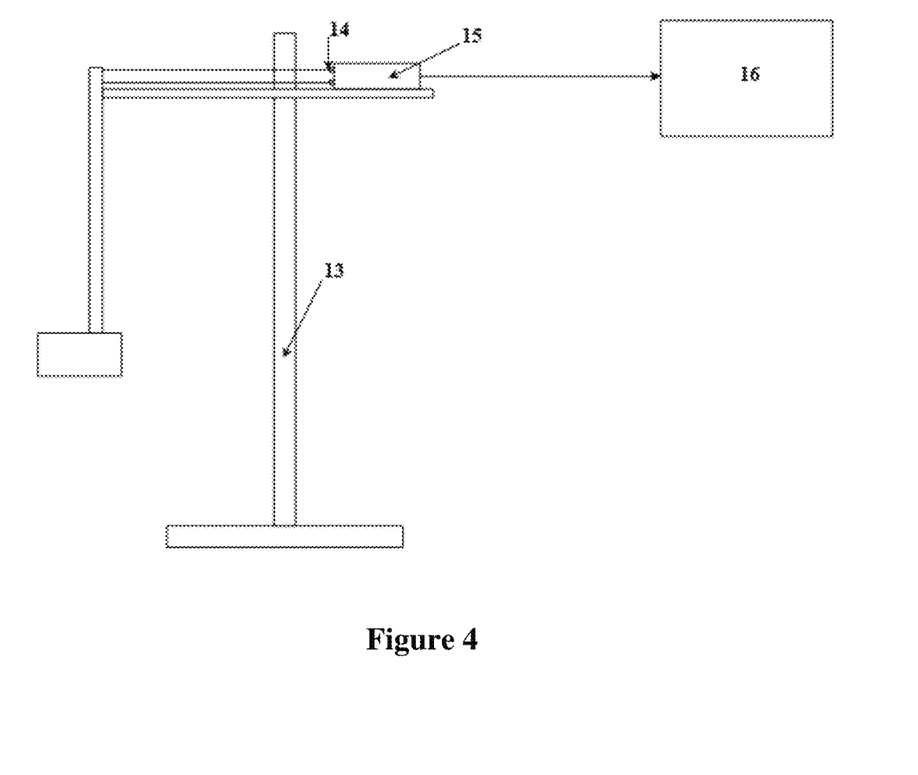

Fixturing elements 5 are used to attach the device (FIG. 4) to a holder 13, which is used to immerse said device into the electrolyte and to control its immersion depth. The temperature sensors of the device communicate with a system for registration, data processing, and visualization of obtained results comprised of a digital temperature meter 15 and a tablet computer 16 by means of connectors 14. The digital temperature meter records the time dependencies of electrolyte and reference material temperatures. The digital temperature meter communicates via USB and/or Wi-Fi channels with the computer 16, preferably being the tablet computer, that performs data processing and imaging the measurement results.

When taking measurements, the metal body 1 according to any of the device embodiments (FIGS. 1-3) is immersed into the electrolyte, as a result of which the melt fills the electrolyte sampling receptacles 7. The metal body is held in the melt until the readings of thermocouples within the electrolyte sample 8 and the reference material 9 become equal, and then it is removed from the melt. Immersion of the device metal body into the electrolyte and its removal therefrom, as well as immersion depth control, are performed with the help of the holder 13. The device metal body is cooled down above the crust on the electrolyte surface, thus, making it possible to obtain more distinct electrolyte phase crystallization peaks by reducing device cooling rate and excluding the influence of external conditions on the measurement results. At the time of cooling down, time dependencies of electrolyte and reference material temperatures are registered using a measuring system including the digital temperature meter 15 communicated with the tablet computer 16. The device metal body cools down to the temperature below the electrolyte solidus temperature. Once measurements are taken, the device metal body is immersed into the melt where it is held until the melt temperature is achieved, following which the device is removed from the melt and the electrolyte sample is poured out. Studies show that for accurate data at least three cooling curves must be registered. The number of device immersions into an electrolyte is defined based on the device metal body design.

Once measurements are finished, the thermal curve of sample temperature as a function of cooling time (($T_2$, $T_3$, $T_4$)=$f(\tau)$) and the differential-thermal curve of a sample and reference material temperature difference as a function of cooling time (($\Delta T$)=$f(\tau)$) are drawn. In order to evaluate phase content in an electrolyte sample, a phase crystallization temperature on the thermal curve and respective peaks on the differential-thermal curve should be determined and the measurement results should be compared with X-ray phase analysis results. After that calibration, dependencies of the peak parameters (half-width/area/height) on respective phase contents shall be plotted. Plotted calibration dependencies are used to determine the phase content in samples of an electrolyte the content of which is within the boundaries of the content of calibration samples.

Method sensitivity is limited by the phase concentration in an electrolyte and is no less than 3 wt %. If a phase concentration in an electrolyte is less than 3 wt %, it becomes difficult to identify this phase because a phase peak on the differential-thermal curve is not observed.

Figure 5:
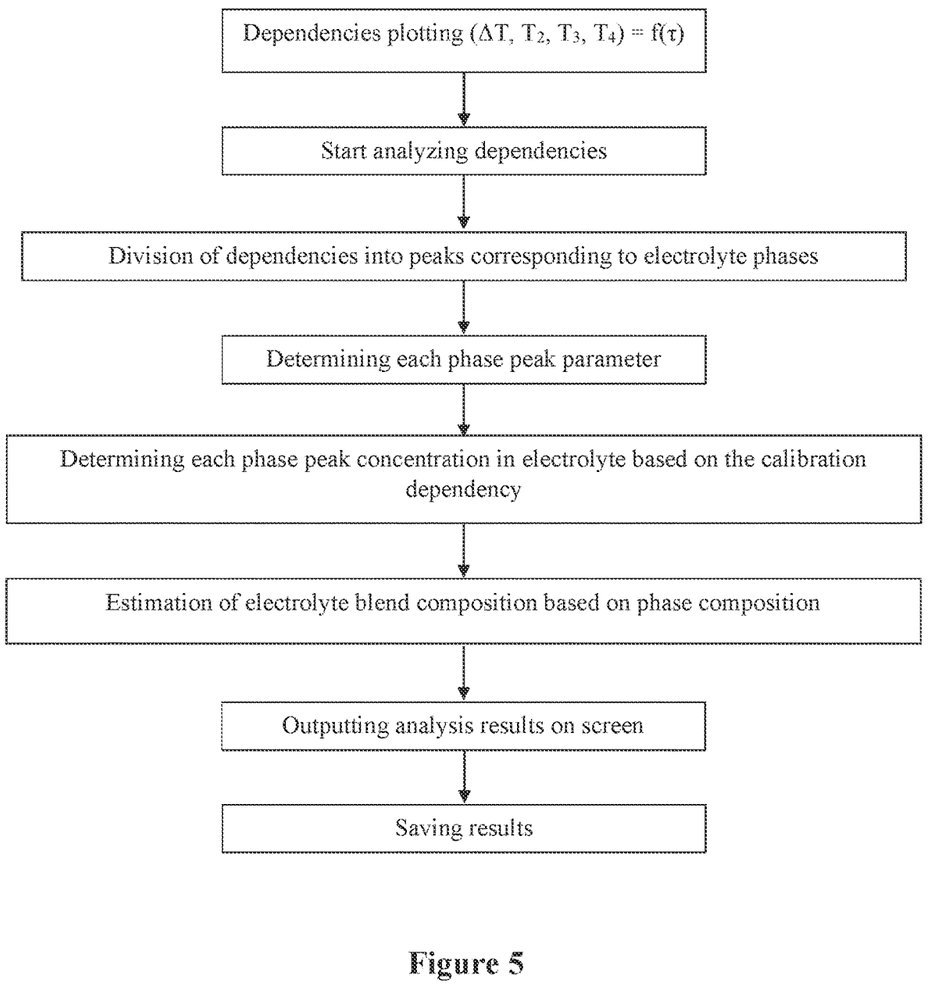
FIG. 5 shows a block diagram of a data processing sequence.

Processing of measurement results includes following operations (FIG. 5):

1. Dependencies plotting ($\Delta T$, $T_2$, $T_3$, $T_4$)=f($\tau$).
2. Division of obtained dependencies into peaks corresponding to electrolyte phases.
3. Determining of each phase peak parameters (height and/or area and/or half-width of a phase peak).
4. Determining of each phase peak concentration in electrolyte based on the calibration dependency on one of the phase peak parameters.
5. Determining of phase and blend compositions of electrolyte solid samples taking into account all crystallizing phases the content of which in the electrolyte sample is no less than 3 wt %.

A method for electrolyte composition analysis includes following steps.

1. Immersing a device metal body into an electrolyte melt and its holding herein until electrolyte sample and reference material temperatures become equal.
2. Removing the device metal body having receptacles filled with electrolyte samples from the melt and its cooling down above the electrolyte crust up to the temperature below the melt solidus temperature according to a thermocouple registering the temperature in the electrolyte sample.
3. Registering time dependencies of electrolyte and reference material cooling down.
4. Repeating the immersion of the device metal body into the melt for electrolyte washing out.
5. Analyzing obtained differential-thermal curves in order to determine the liquidus temperature, the electrolyte superheating value, and electrolyte phase crystallization temperatures.
6. Determining electrolyte phase and blend compositions.

The implementation of the claimed method is supported by examples.

EXAMPLE 1

For electrolytes of the NaF—AlF$_3$—KF—CaF$_2$—Al$_2$O$_3$ system having a molar ratio NaF/AlF$_3$ (cryolite ratio) which comprise no less than 4 wt % of potassium fluoride and 4 wt % of calcium fluoride, the main electrolyte phases are cryolite, elpasolite, chiolite, calcium-containing combinations, and alumina (Al$_2$O$_3$). All measurements were taken with a device comprising one electrolyte sample receptacle. Time of device cooling above the crust on the electrolyte surface was 8 min, accordingly, the average cooling rate was 50 deg/min. In addition, measurements were taken with a device comprising three electrolyte sample receptacles. Time of device cooling above the crust on the electrolyte surface was 11 min, accordingly, the average cooling rate was 36 deg/min. The typical curves obtained based on the measurements are shown in FIG. 6.

Figure 6:
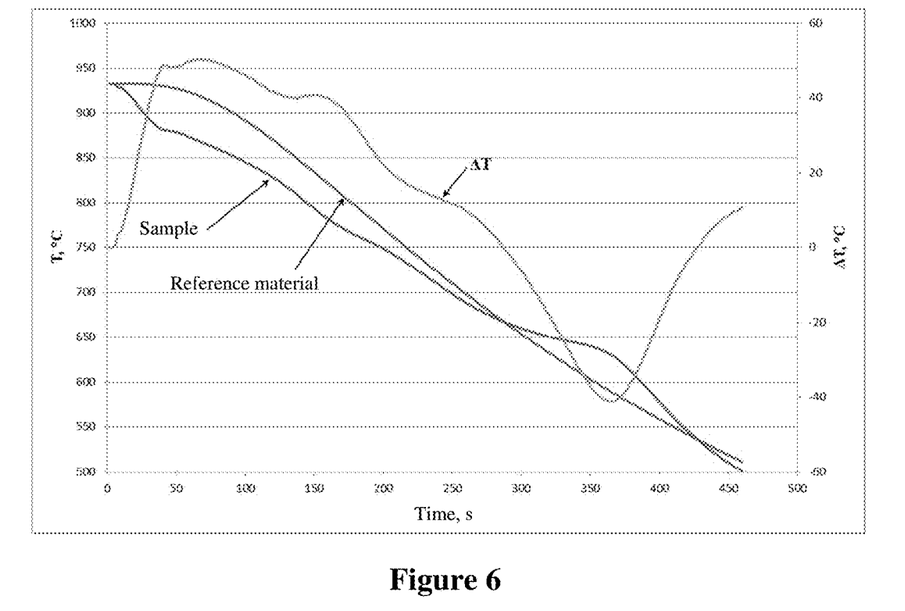
FIG. 6 shows typical thermal curves of sample and reference material temperatures as a function of cooling time, and a differential-thermal curve of a sample and reference material temperature difference as a function of cooling time.
Figure 7:
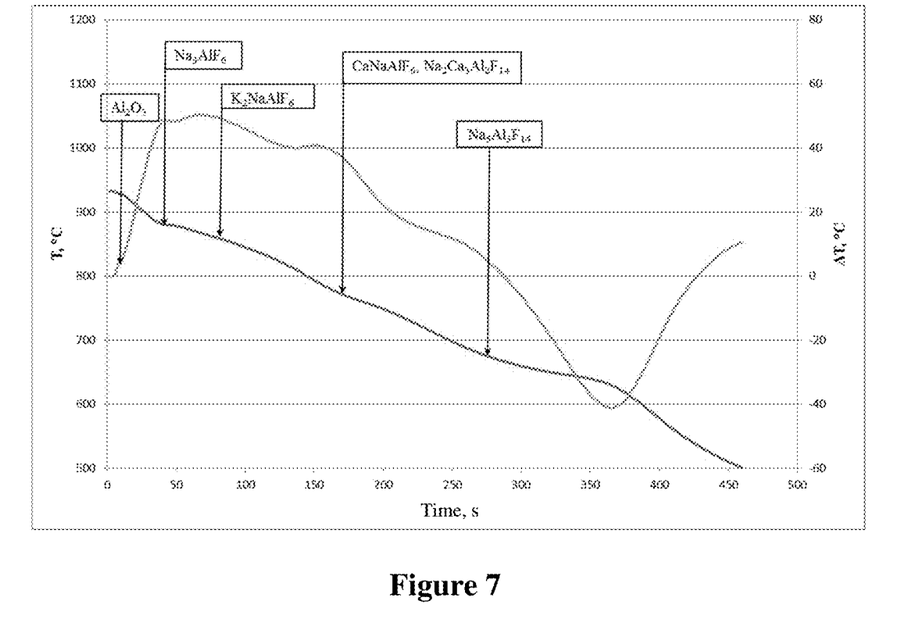
FIG. 7 shows an example of determining the arrangement of electrolyte phase crystallization peaks on a thermal curve of a sample temperature as a function of cooling time and differential-thermal curve of a sample and reference material temperature difference as a function of cooling time.
Figure 8:
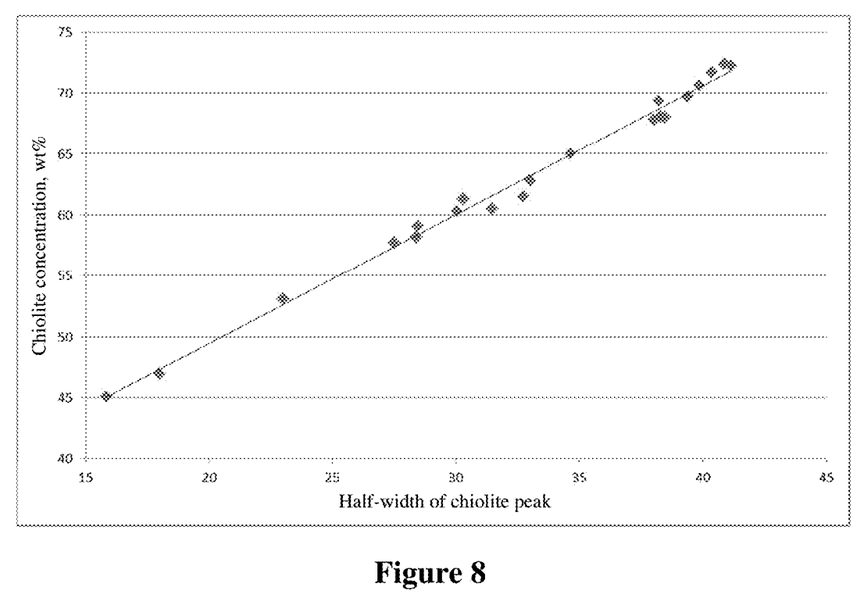
FIG. 8 shows a calibration dependence of chiolite concentration ($Na_5Al_3F_{14}$) on its peak half-width.
Figure 9:
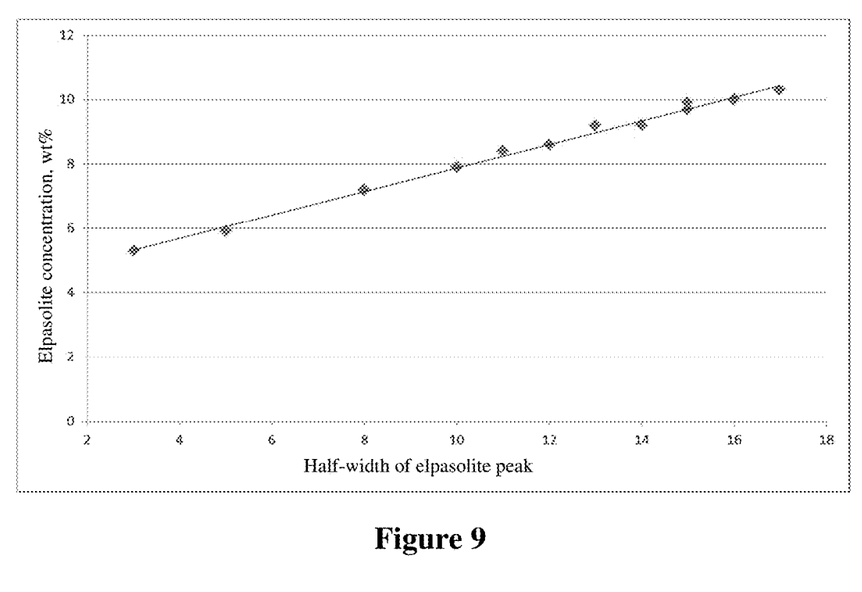
FIG. 9 shows a calibration dependence of elpasolite concentration ($K_2NaAlF_6$) on its peak half-width.
Figure 10:
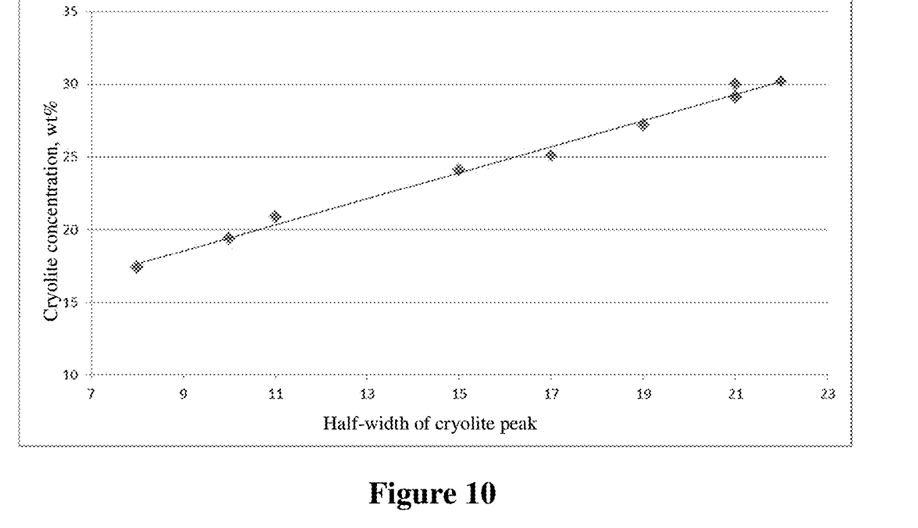
FIG. 10 shows a calibration dependence of cryolite concentration ($Na_3AlF_6$) on its peak half-width.
Figure 11:
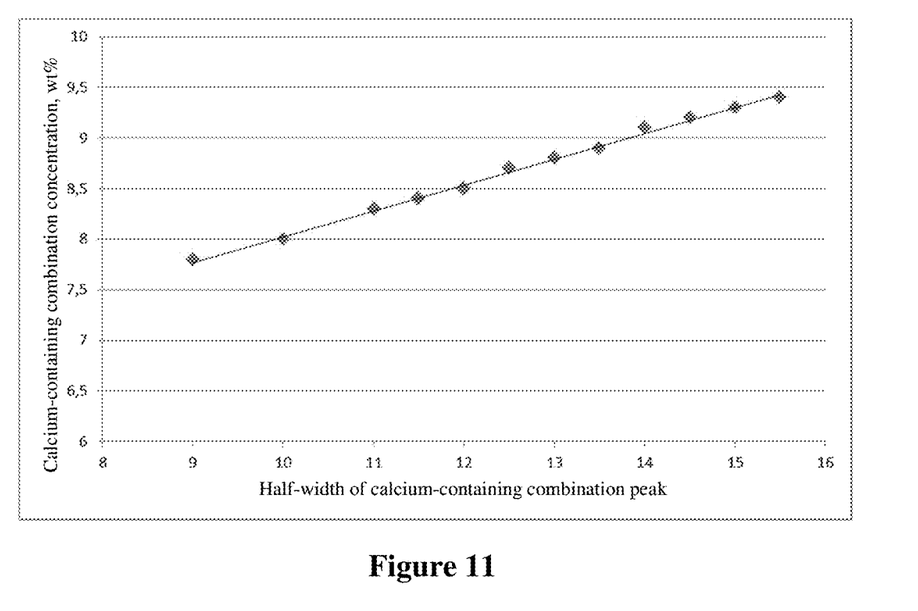
FIG. 11 shows a calibration dependence of the concentration of Ca-containing phases ($CaNaAlF_6$ and $Na_2Ca_3Al_2F_{14}$) on their peak half-width.

When analyzing the registered differential-thermal and thermal curves, positions of five peaks on the differential-thermal curve and respective peaks on the thermal curve were determined and the measurement results were compared with the X-ray phase analysis results (FIG. 6). The phase crystallization temperature was determined based on a projection onto the temperature curve of the straight-line portion start (a drop) on the differential-thermal curve of a sample and reference material temperature difference as a function of time. In addition, it is possible to use a combined representation of measurement results, which is a dependency of a sample, and reference material temperature difference on the electrolyte temperature. Once electrolyte phase crystallization temperatures had been determined, the liquidus and solidus temperatures and the electrolyte superheating value were determined.

Once electrolyte phase crystallization temperatures in the given electrolyte composition had been determined, a half-width of each phase peak was determined on the differential-thermal curve. To analyze an electrolyte composition the calibration dependencies between phase concentrations in the electrolyte and a half-width of a corresponding peak are used. Examples of these dependencies for the NaF—AlF$_3$—KF—CaF$_2$—Al$_2$O$_3$ system are illustrated in FIGS. 7-11. Once the electrolyte phase composition had been determined, its blend composition and a cryolite melt ratio value were estimated. Tables 1-4 illustrate main electrolyte phases obtained by X-ray phase analysis (XRA) and by analysis of differential-thermal curves according to the claimed method (DTA). In addition, these tables illustrate average deviation values (ad) between analysis results and a mean-square deviation value (MSD).

TABLE 1

| Cryolite concentration, wt % | | Deviation |
|---|---|---|
| DTA | XRA | $\Delta$ |
| 27.5 | 27.2 | +0.3 |
| 29.3 | 29.1 | +0.2 |
| 20.3 | 20.9 | −0.6 |
| 17.6 | 17.4 | +0.2 |
| 19.4 | 19.7 | −0.3 |
| 29.3 | 30 | −0.7 |
| 23.9 | 24.1 | −0.2 |
| | ad | −0.16 |
| | MSD | 0.4 |

TABLE 2

| Elpasolite concentration, wt % | | Deviation |
|---|---|---|
| DTA | XRA | $\Delta$ |
| 5.3 | 5.3 | 0 |
| 6.0 | 5.9 | +0.1 |
| 7.1 | 7.2 | −0.1 |
| 7.9 | 7.9 | 0 |
| 9.3 | 9.2 | +0.1 |
| 9.7 | 9.7 | 0 |
| 10.1 | 10 | +0.1 |
| 10.4 | 10.3 | +0.1 |
| 10.8 | 10.8 | 0 |
| 9 | 9 | 0 |
| | ad | 0.03 |
| | MSD | 0.07 |

TABLE 3

| Ca-containing phase concentration, wt % | | Deviation |
|---|---|---|
| DTA | XRA | $\Delta$ |
| 8.3 | 8.3 | 0 |
| 8.6 | 8.4 | +0.2 |
| 8.3 | 8.3 | 0 |
| 8.6 | 8.5 | +0.1 |
| 8.9 | 8.7 | +0.2 |
| 8.9 | 8.8 | +0.1 |

TABLE 3-continued

| Ca-containing phase concentration, wt % | | Deviation |
|---|---|---|
| DTA | XRA | Δ |
| 7.7 | 7.8 | +0.1 |
| 8 | 8 | 0 |
| 9.2 | 9.1 | +0.1 |
| 9.4 | 9.3 | +0.1 |
| | ad | 0.09 |
| | MSD | 0.074 |

TABLE 4

| Chiolite concentration, wt % | | Deviation |
|---|---|---|
| DTA | XRA | Δ |
| 45.0 | 45.1 | −0.1 |
| 47.3 | 47.0 | +0.3 |
| 52.6 | 53.1 | −0.5 |
| 57.4 | 57.7 | −0.3 |
| 58.3 | 58.2 | +0.1 |
| 58.4 | 59.1 | −0.7 |
| 60.1 | 60.3 | −0.2 |
| 60.3 | 61.3 | −1.0 |
| 63.2 | 62.8 | +0.4 |
| 68.8 | 68.1 | +0.7 |

TABLE 4-continued

| Chiolite concentration, wt % | | Deviation |
|---|---|---|
| DTA | XRA | Δ |
| 68.7 | 69.4 | −0.7 |
| 69.9 | 69.7 | +0.2 |
| 70.4 | 70.6 | −0.2 |
| 71.5 | 72.4 | −0.9 |
| 71.8 | 72.2 | −0.4 |
| 68.5 | 67.8 | +0.7 |
| 68.9 | 68 | +0.1 |
| 62.9 | 61.5 | +1.4 |
| 64.9 | 65 | −0.1 |
| 61.6 | 60.5 | +1.1 |
| | ad | −0.005 |
| | MSD | 0.643 |

Table 5 illustrates data for phase and blend compositions obtained by X-ray phase analysis and by analysis of differential-thermal curves according to the claimed method. Compositions 1-4 were determined using a device having one electrolyte sampling receptacle; compositions 5-7 were determined using a device having three electrolyte sampling receptacles. It can be seen that the mean-square deviation value of analysis results is no more than 0.892. Accordingly, the claimed device and a method provide a reasonable determination of electrolyte phase and blend compositions.

TABLE 5

Comparison of phase and blend compositions obtained by different methods

| | Composition 1 | | | Composition 2 | | | Composition 3 | | | Composition 4 | | |
|---|---|---|---|---|---|---|---|---|---|---|---|---|
| | DTA | XRA | Δ | DTA | XRA | Δ | DTA | XRA | Δ | DTA | XRA | Δ |
| Cryolite | 25.7 | 25.1 | 0.6 | 14.5 | 14.6 | −0.1 | 29.3 | 29.1 | 0.2 | 17.6 | 17.8 | −0.2 |
| Elpasolite | 10.8 | 10.8 | 0 | 9.7 | 9.9 | −0.2 | 9.0 | 9 | 0 | 8.2 | 8.2 | 0 |
| Ca-phases | 8.9 | 9 | −0.1 | 8.9 | 8.7 | 0.2 | 9.4 | 9.3 | 0.14 | 9.4 | 9.4 | 0 |
| Chiolite | 48.3 | 47.9 | 0.4 | 60.1 | 60.3 | −0.24 | 46.2 | 45.8 | 0.4 | 58.3 | 58.8 | −0.5 |
| KF | 6.1 | 6.16 | −0.06 | 5.48 | 6.01 | −0.53 | 5.07 | 5.26 | 0.19 | 4.65 | 4.9 | −0.25 |
| $CaF_2$ | 4.6 | 4.26 | 0.34 | 4.6 | 4.42 | 0.18 | 4.91 | 4.68 | 0.23 | 4.91 | 4.6 | 0.31 |
| NaF | 41.56 | 41.16 | 0.4 | 40.04 | 40.4 | 0.36 | 42.91 | 42.31 | 0.6 | 41.21 | 41.3 | 0.09 |
| $AlF_3$ | 46.16 | 45.67 | 0.49 | 47.79 | 48.42 | 0.63 | 46.01 | 45.49 | 0.52 | 47.75 | 47.88 | 0.13 |
| KO | 1.8 | 1.79 | 0.01 | 1.68 | 1.66 | 0.02 | 1.87 | 1.85 | 0.02 | 1.73 | 1.72 | 0.01 |

| | Composition 5 | | | Composition 6 | | | Composition 7 | | | Deviation | |
|---|---|---|---|---|---|---|---|---|---|---|---|
| | DTA | XRA | Δ | DTA | XRA | Δ | DTA | XRA | Δ | ad | MSD |
| Cryolite | 19.4 | 19.4 | 0 | 20.3 | 20.1 | 0.2 | 19.4 | 19.5 | 0.1 | 0.086 | 0.273 |
| Elpasolite | 9.3 | 9.3 | 0 | 9.0 | 9.1 | 0.1 | 9.0 | 8.8 | 0.20 | −0.014 | 0.121 |
| Ca-phases | 9.4 | 9.4 | 0 | 9.7 | 9.9 | 0.2 | 9.7 | 9.2 | 0.5 | 0.071 | 0.229 |
| Chiolite | 56.3 | 56.2 | 0.1 | 55.8 | 55.2 | 0.6 | 54.8 | 56.8 | 2.0 | −0.171 | 0.892 |
| KF | 5.27 | 5.35 | 0.08 | 5.07 | 5.25 | 0.18 | 5.07 | 5.11 | 0.04 | −0.19 | 0.169 |
| $CaF_2$ | 4.91 | 4.61 | 0.3 | 5.06 | 4.78 | 0.28 | 5.06 | 4.53 | 0.53 | 0.31 | 0.111 |
| NaF | 41.41 | 41.37 | 0.04 | 41.76 | 41.27 | 0.49 | 40.68 | 41.47 | 0.79 | 0.041 | 0.502 |
| $AlF_3$ | 47.76 | 47.46 | 0.3 | 47.84 | 47.18 | 0.66 | 46.91 | 47.47 | 0.56 | 0.093 | 0.533 |
| KO | 1.73 | 1.74 | 0.01 | 1.75 | 1.74 | 0.01 | 1.74 | 1.74 | 0 | 0.009 | 0.011 |

We claim:

1. A device for molten electrolyte composition analysis, the device comprising:
   a metal body comprising a compartment with a reference material arranged therein and at least one receptacle containing an electrolyte sample, wherein an α-modification of aluminum oxide is used as the reference material;
   at least one first temperature sensor having a sensing end that is immersed into the reference material and at least one second temperature sensor having a sensing end that is immersed into the electrolyte sample, wherein the first temperature sensor's sensing end is entirely encased in a corundum cover; and
   a data processing system configured to communicate with the at least one first temperature sensor and the second temperature sensor, to calculate and plot thermal and differential-thermal curves based on data received from the first temperature sensor and the second temperature sensor, determine phase crystallization temperatures of the reference material and the electrolyte sample on the thermal and differential-thermal curves, and to calculate a composition of the electrolyte sample based on the phase crystallization temperatures and a pre-calibration carried out based on phase crystallization temperatures in electrolytes of a known composition.

2. The device according to claim 1, characterized in that the metal body comprises from one to four electrolyte sampling receptacles, wherein if the number of receptacles is more than one they are arranged on different sides of the compartment for reference material.

3. The device according to claim 1, characterized in that thermocouples are used as the temperature sensors.

4. The device according to claim 1, characterized in that it comprises a metal protective tube rigidly connected to the metal body around the periphery of the reference material compartment, wherein holders and fixing members for the temperature sensors to be immersed directly into the electrolyte sampling receptacles are arranged on the tube.

5. The device according to claim 4, characterized in that electrolyte temperature sensors are arranged within the metal tube rigidly connected to the metal body, wherein the metal tube is connected, via through-channels made in the metal body, to the electrolyte sampling receptacles for enabling immersion of the temperature sensors into the electrolyte sampling receptacles.

6. A method for molten electrolyte composition analysis, comprising:
   immersing a device into a molten electrolyte, wherein the device comprises a compartment containing a reference material and at least one receptacle that the molten electrolyte fills when the device is immersed;
   using a first temperature sensor to read a first temperature data of the molten electrolyte;
   using a second temperature sensor to read a second temperature data of the reference material;
   removing the device from the molten electrolyte and cooling down the device having the at least one receptacle filled with the molten electrolyte;
   using the first temperature sensor to read a third temperature data of the molten electrolyte;
   using the second temperature sensor to read a fourth temperature data of the reference material;
   communicating the first temperature data, the second temperature data, the third temperature data, and the fourth temperature data to a data processing system;
   using the data processing system to draw differential-thermal curves based the first temperature data, the second temperature data, the third temperature data, and the fourth temperature data; and
   using the data processing system to divide the differential-thermal curves into phase peaks; and
   using the data processing system to analyze the phase peaks to determine phase and blend composition information for the molten electrolyte.

7. The method according to claim 6, wherein the device is cooled down above a crust on the molten electrolyte surface.

8. A method for molten electrolyte composition analysis, comprising:
   immersing a device into a molten electrolyte, wherein the device comprises a compartment containing a reference material and at least one receptacle that the molten electrolyte fills when the device is immersed, such that the at least one receptacle fills with at least one electrolyte sample;
   holding the device in the molten electrolyte until the temperatures of the at least one electrolyte sample and the reference material become equal based on readings from at least one first temperature sensor immersed in the reference material and at least one second temperature sensor immersed in the at least one electrolyte sample;
   removing the device having the at least one receptacle filled with the at least one electrolyte sample from the molten electrolyte and cooling down the device to a temperature lower than the solidus temperature of the at least one electrolyte sample;
   using a data processing system to register time dependencies for cooling the reference material and the at least one electrolyte sample, plot one or more thermal curve of dependence of the at least one electrolyte sample's temperature against cooling time, and plot one or more differential-thermal curves of dependence of the temperature difference between the at least one electrolyte sample and the reference material against time;
   using the data processing system to determine the phase crystallization temperature on the one or more thermal curves and corresponding peaks on the one or more differential-thermal curves, wherein the phase crystallization temperature is determined based on the projection of the beginning of a straight section of the differential-thermal curve on the thermal curve;
   using the data processing system for determining one or more phase peak parameters selected from a group consisting of the height of the phase peaks, the area of the phase peaks, and the half-width of the phase peaks, determining the concentration of the phases in the electrolyte based on a pre-determined calibration dependence, which is based on phase crystallization temperatures in electrolytes of a known composition, on at least one of the phase peak parameters;
   using the data processing system for determining the liquidus temperature and the superheat of the electrolyte and determining the phase and component composition of the at least one electrolyte sample, including all crystallizing phases, the content of which is no less than 3 wt-% in the at least one electrolyte sample.

9. The method according to claim 8, wherein the device is cooled down above a crust on the molten electrolyte surface.

* * * * *